United States Patent [19]

Nagata et al.

[11] Patent Number: 4,707,613

[45] Date of Patent: Nov. 17, 1987

[54] INSPECTING DEVICE FOR A THIN FILM COATING MATERIAL WITH APPLICATOR-FOLLOWING DETECTOR

[75] Inventors: Tsuyoshi Nagata; Katsuto Fujita, both of Takatsuki, Japan

[73] Assignee: Sunstar Engineering Inc., Osaka, Japan

[21] Appl. No.: 849,420

[22] Filed: Apr. 8, 1986

[30] Foreign Application Priority Data

Apr. 18, 1985 [JP] Japan ................................ 60-83249

[51] Int. Cl.⁴ ........................................... G01N 21/88
[52] U.S. Cl. .................................... 250/572; 356/444
[58] Field of Search ............... 250/562, 563, 571, 572; 356/434, 435, 444, 445

[56] References Cited

U.S. PATENT DOCUMENTS

| | | | |
|---|---|---|---|
| 3,614,241 | 10/1971 | Sanford | 356/444 |
| 3,754,146 | 8/1973 | Chow | 250/563 |
| 3,840,302 | 10/1974 | Brunton et al. | 250/563 |
| 4,274,747 | 6/1981 | Van Beeck et al. | 356/434 |

*Primary Examiner*—David C. Nelms
*Attorney, Agent, or Firm*—Koda and Androlia

[57] ABSTRACT

An inspecting device for inspecting a thin film coating material applied to a material being treated such as glass includes a projector and a photoreceptor disposed across the material being treated, a manipulator for enabling relative movement of these projector and photoreceptor along the coating material applied to the material being treated, and an electric circuit part for producing a control signal when output of the photoreceptor exceeds a specified value.

4 Claims, 7 Drawing Figures

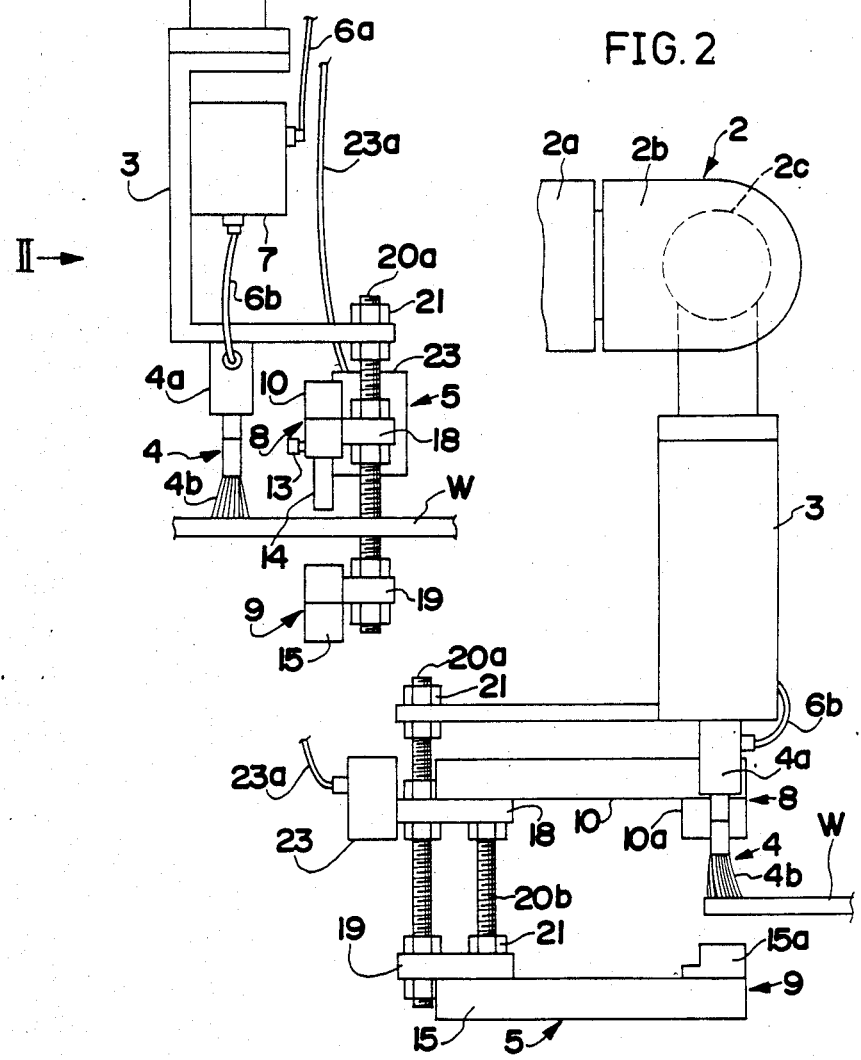

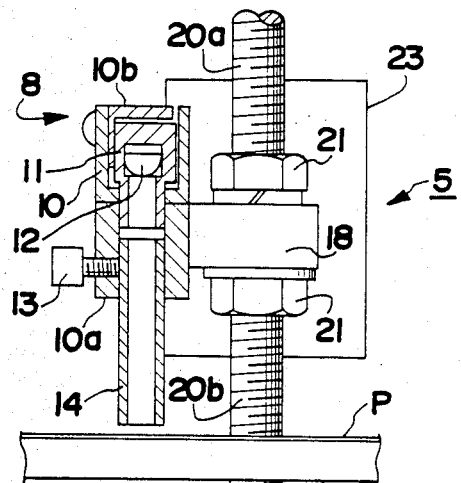
FIG. 3
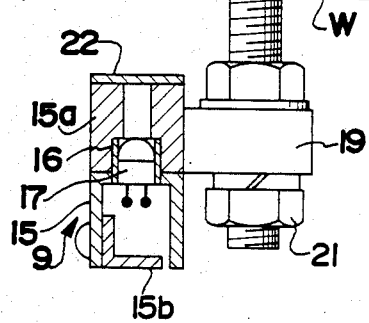
FIG. 4
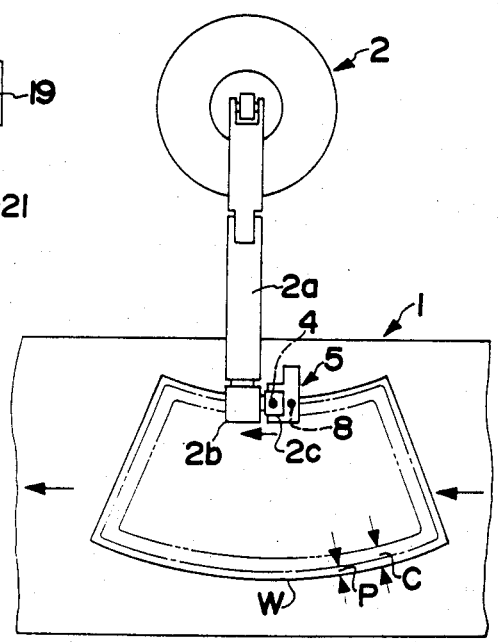

INSPECTING DEVICE FOR A THIN FILM COATING MATERIAL WITH APPLICATOR-FOLLOWING DETECTOR

BACKGROUND OF THE INVENTION

The present invention relates to an inspecting device for inspecting a thin film coating material applied to a material being treated. The device is, for example, employed for examining the quality of primer applied to peripheral portions of front glass, rear glass and the like of an automobile.

In assembling processes of the automobile, window glass such as front and rear glass is mounted to a window frame of an automobile body after its entier periphery is coated with a sealing material. Furthermore, prior to an application of the sealing material, black primer is applied to a surface of the window glass and the window frame so as to enhance the reliability of adhesion therebetween. Such an applying work of the sealing material and the primer utilizes a variety of types of manipulators, thus being automated.

These coating materials, however, usually vary a great deal in fluidity, surface condition and the like with temperature, or depending on whether or not they have contact with air, or the like. Also, the coated materials vary in applied condition with the used quantity, the applying speed, or the like. Consequently, it becomes relatively difficult to achieve the quantitative control of the materials in the coating process and to apply the materials in a constant state. Thus, the normal coating is not always expected. For example, there will often arise a problem that the applied primer has sheer portions because of its insufficient film thickness or that the coating per se becomes blurred owing to the insufficient amount of the primer used.

In the meantime, while the coating work is automated, as regards examining work an operator still directly of indirectly, for example through ITV (Industrial Television), see whether or not the coating is normally performed. Accordingly, as a result of the change of the operator's criterion, the quality of the coating is subject to irregularity and also examination errors are liable to occur. Besides, the labor spent on such examining work results in an increase in cost. Furthermore, since window glass that has undergone a black ceramic treatment on its peripheral portion is increasingly employed nowadays, it becomes almost impossible to examine with man's eyes the condition of the black primer being applied.

It is true that ITV may be utilized to effect an automatic examination, nevertheless difficulties are encountered in such examination because of the fact that the black ceramic treatment and the primer are identical in color. In addition to that there exists the problem that the high cost is involved since ITV is of comparatively large size and signal operations thereof are complicated.

SUMMARY OF THE INVENTION

The present invention is made with a view to solving the aforementioned problems.

Hence an objective of the invention is to provide a simple and small-sized inspecting device for inspecting the quality of the thin film coating material applied to a material being treated, particularly the quality of black primer applied to window glass that has undergone the black ceramic treatment.

Another objective of the invention is to provide a coating device that permits the automation of an inspecting operation as well as a coating operation and at the same time effect these two operations substantially simultaneously in the same process.

Other objectives and features of the invention will be more apparent from the following description and appended drawings.

BRIEF DESCRIPTION OF THE DRAWINGS

FIG. 1 is a front view showing an inspecting device according to an embodiment of the invention;

FIG. 2 is a side view as viewed from an arrow II of FIG. 1;

FIG. 3 is an enlarged sectional front view showing a photosensor apparatus of FIG. 1;

FIG. 4 is a general schematic plan view showing the inspecting device of the invention;

DETAILED DESCRIPTION OF THE PREFERRED EMBODIMENT

Figure 5:
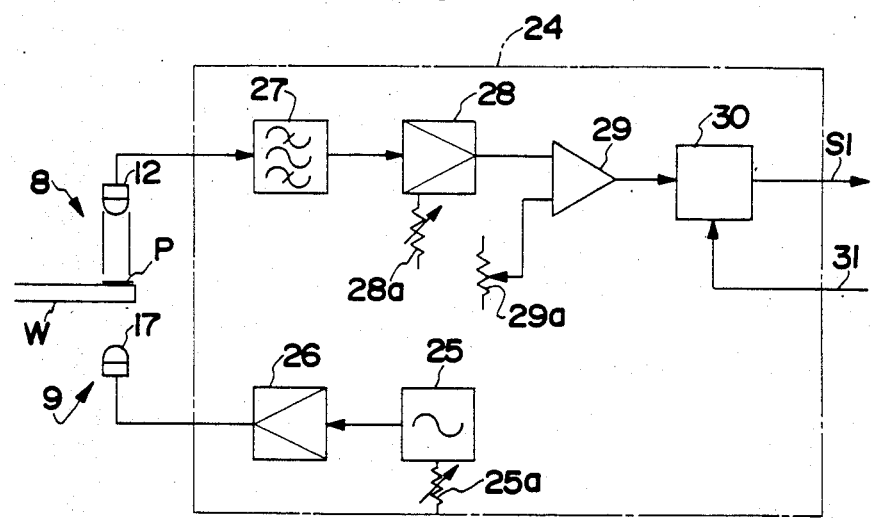
FIG. 5 is a block diagram illustrating an embodiment of an electric circuit part of the inspecting device.

There is described below an embodiment of the coating device according to the present invention that is adapted to apply black primer to a surface of front grass in the automobile and further to inspect it.

In FIG. 4, work W of front glass that has undergone a black ceramic treatment C on its periphery is successively transported on an intermittently operating conveyor 1. The work W is positioned and stationary in a station for the process of coating black primer. In this station is disposed a coating device composed of a multi-articulated robot 2, which is adapted to apply black primer P in a fixed width to the entire periphery of the upper surface of work W as shown by a chain line and to automatically ascertain whether or not the coating is normally attained.

Also with reference to FIGS. 1 through 3, the robot 2 has a rotary wrist 2b and a bent wrist 2c at the end of an arm 2a. The lower flange portion of the wrist 2c is provided with a brush 4 as a coating means and with a photosensor apparatus 5 as an inspecting means through a bracket 3. The brush 4 is made of a hollow core material and a number of hairs disposed therearound.

Primer is pressingly sent from a coating material feeder of pressure type not shown through tubes 6a and 6b, and a valve 7. The primer then flows into abase part 4a of the brush 4 and passes through a hollow part and next percolates from a hair part 4b, so that it can be applied to the surface of the work W undergone the black ceramic treatment to thereon form its film approximately several millimeters in width, and ten and several $\mu$ meters in thickness.

The photosensor apparatus 5, which is positioned at a specified distance from behind the brush 4, is provided for the purpose of examining the condition of the primer applied by the brush 4. A photoreceptor 8 and a projector 9 are provided vertically across the work W so as to detect a change of the amount of light received by the photoreceptor 8 which depends upon the film condition of the primer. The photoreceptor 8 has a photodetector 12 held in a cylindrical holder 11 at the end of a photo-reception arm 10, and a light-excluding bobbin 14 to be fixed by an adjusting screw 13. Meanwhile, the projector 9 has a light-emitting element 17 held in a cylindrical holder 16 at the end of a projection arm 15. For the photodetector 12 a photodiode, phototransistor, or the like is employed, while for the light-emitting element a light-emitting diode, an electric bulb, or the like is used.

The photoreception arm 10, and the projection arm 15 are respectively secured to mounting bases 18 and 19 at each of base portions thereof. These bases 18 and 19 are mounted with the bracket 3 by bolts 20a and 20b, a nut 21, etc. in a manner to be adjustable for their relative heights.

Besides, reference marks 10a and 15a individually designate respective holder parts installed at the ends of the photoreception arm 10 and the projection arm 15; 10b, 15b covers; 22 a transparent cover; 23 a relay box; and 23a an electric wire.

FIG. 5 is a block diagram illustrating the relay box 23 and an electric circuit part 24 provided in a control box not shown. In FIG. 5, the frequency of a drive part 26 is modulated by an osicillator 25 that is capable of regulating the frequency at about several KHz so as to cause the light-emitting element 17, e.g. the light-emitting diode in this case, to emit light. Out of the output from the photodetector 12 a light-component from the light-emitting element alone is passed and recovered by means of a bandpass filter 27, and then amplified to a suitable level by an amplifier 28.

Thereafter this signal is compared with a reference value by a comparator 29. Where the output from the amplifier 28 is larger than the reference value, that is, the amount of light received by the photodetector 12 is larger than a reference amount, the comparator 29 actuates an output part 30 to yield an on-off control signal S1. An external input 31 is provided to forcibly set the control signal S1 in an off-state. The function of the external input 31 is to prevent any unnecessary control signal S1 from being produced where the photodetector 12 is in a position unsuitable to examine the primer on the work W as described below (since such a situation is usually determined by the control condition of the robot 2, a signal can be produced by a control circuit of the robot 2.)

Besides, reference marks 25a, 28a, and 29a respectively designate frequency, amplifaction and reference value regulators.

Nor there is given a description below as to how the robot 2 operates, and more particularly as to how the brush 4 and the photosensor apparatus 5 are controled for their positions relative to the work W.

Firstly the primer in specified width and thickness is applied onto the work W placed at a predetermined position after the brush 4 moves on the whole periphery and along the surface of the work. To this end, adjustments are made in advance to the flow rate and temperature of the primer that is pressingly fed through the tubes 6a and 6b, to the on-off timing of the valve 7, and to the pressing degree and speed of the hair part 4b of the brush 4 against the work W.

The, the end of the light-excluding bobbin 14 of the photsensor apparatus 5 is, kept at a specified slight distance from a surface of the work W, moved along the primer P thus applied thereon by the brush 4. In order to do this, the photoreceptor 8 and the projector 9 are adjusted for their heights by means of the bolts 20a and 20b, and also the nut 21, and the light-excluding bobbin 14 is adjusted for its degree of insertion into the holder part 10a as well. Further the robot 2 is given an instruction or a program to make such a specified movement as mentioned above.

Figure 6:
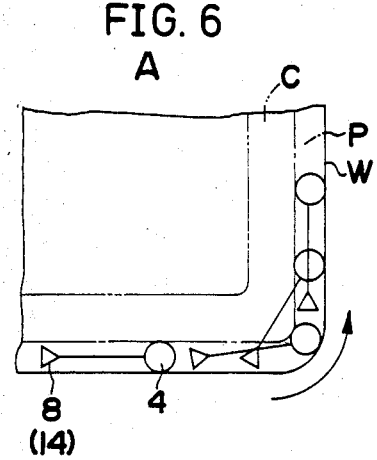
FIGS. 6A and 6B are views respectively illustrating examples of movement of the photosensor apparatus in a corner portion of work.
Figure 6:
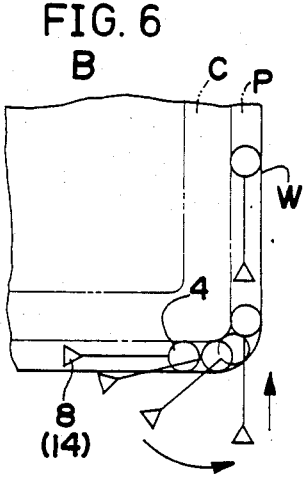

Referring to the movement in a corner portion of the work W, the brush 4 and the light-excluding bobbin 14 can move to leave the same trace as shown in FIG. 6A even at slightly different speeds where the hair part 4b is circular in section as in this embodiment and hence the brush 4 has no option of proceeding directions.

On the contrary, the brush 4 is rotated at the corner portion to change the direction in which it is moving where the brush 4, which has a hair part 4b great in length or which is of a special shape, has to be unvaribaly going in a specified direction. Accordingly, the light-excluding bobbin 14 goes off the trace of the brush 4 as illustrated in FIG. 6B. In this case, the control circuit of the robot 2 transmits a signal to the external input 31 of the electric circuit part 24 in the photosensor apparatus 5 so that no control signal S1 may be erroneously produced whatsoever.

Though this control signal, the following step against the extraordinary situation is to be taken. Thus, an alarm lamp or buzzer is actuated, the robot is stopped, irregular portions detected are coated again, or the whole faulty work W is removed from a main line, or the like.

Now referring to the detailed working of the device, when the work W, transported by the conveyor 1, is put in a specified position, the robot 2 actuates the brush 4 to move to a coating-start point, and the valve 7 is opened. Then the brush 4, making a predetermined trace on the work W, applies the primer P thereon and at the same time the photosensor apparatus 5 inspects the primer thus applied. When sheer or blurred portions are detected in the primer, a control signal S1 is produced so that an extraordinary alarm is sounded and a predetermined step is taken.

In the photosensor apparatus 5, light emitted by the light-emitting element 17 passes through the cover 22, and further upwardly through the work W, and then through the light-excluding bobbin 14 does it reach the photodetector 12, in which the light is converted into an electric signal corresponding its amount. At this time, the black ceramic treatment C on the work W and the primer P applied thereon exclude the light traveling through the work and thus the amount of light having reached is reduced.

However, the more sheer or blurred portions the applied primer has, or the less wide it is, the larger is observed to be the amount of light passed through the work W than the normal amount. Thus, the light to pass through the work is reduced to several percentages by the black ceramic treatment C, and eventually reduced to several tenths by the primer. Accordingly, it can be even detected that such a slight amount of light having passed varied according to the condition of the primer P.

The boundary value between normal and abnormal values is determined by the regulator 29a. The external input 31 inhibits any control signal S1 from being yielded when the coating work is started, or when the photosensor apparatus 5 is incapable of normally exercising the inspection of the primer P as shown in FIG. 6B.

In the above embodiment, the brush 4 enables the primer P to be applied on the work W along the predetermined trace or line. Furthermore the photosensor apparatus 5 can inspect the quality of the applied primer P. When it detects that the primer P has irregular portions such as sheer or blurred portions, it produces a signal so that a suitable step may be taken. Since the photosensor apparatus 5 is formed integrally with the brush 4 and arranged to move at a specified distance from behind the brush 4 under the control thereof, it can exercise the inspection of the primer substantially simultaneously with the coating operation of the brush 4.

Accordingly, no special process for inspecting is needed and therefore the required time is reduced to a great extent.

Moreover, the equipment cost and space can be decreased to half, since an additional inspecting robot is unnecessary to install. The required time can be reduced to less than half as compared with cases where a single robot has to alternately carry the brush 4 and the photosensor apparatus 5 to perform its operation. Furthermore, it is extremely easy to take measures against the situation that the extraordinary condition is detected through inspection, and inferior goods of work W can be reduced to the minimum, thereby making it possible to improve the yield.

Since the photosensor apparatus 5 is simple in construction, it can be small-sized and light in weight, and accordingly can be manufactured at a low cost. Besides the electric circuit part 24 can be manufactured in small size at a low cost since the signal operations are easy. In addition, the photosensor apparatus 5 can be given higher precision in that the light-excluding bobbin 14 is capable of excluding any unnecessary diffracted, disturbing or the like light.

In the above embodiment, single photodetector 12 and light-emitting element 17 are employed, but a plurality of photo-detectors and light-emitting elements may be juxtaposed to enlarge the detecting width. A combination of suitable slit and lense may be used to examine the applied width. Detecting can be hardly affected by the distrubing light when infrared light is employed therefor. Instead of the brush 4 may be employed a nozzle roller, or the like. As the robot 2 may be used other kinds of manipulators, which may be adapted to move the work W during coating.

The coating material may be used for paint and adhesive as well as primer. As the work W is employed glass having its periphery undergone the black ceramic treatment, but, needless to say, also may be used glass not undergone such a treatment, in which case black primer to be applied in great width may be substituted for the black ceramic treatment C. It may also be arranged that a part of light emitted by the light-emitting element 17 does not pass through the work W but is received by another photodetector in order to correct with a resulting signal the variation of the amount of light being emitted.

What is claimed is:

1. An inspecting device for inspecting a thin film coating material being applied in a predetermined trace to a material being treated, said inspecting device comprising:

a projector and a photoreceptor disposed across said material being treated;

a manipulator for enabling relative movement of the projector and the photoreceptor along said material being treated;

an electric circuit part for producing a control signal when output of said photoreceptor exceeds a specified value which is indicative of a defect in said thin film coating material applied to said material being treated; and wherein said manipulator is provided with coating means for applying the coating material to said material being treated, and said projector and photoreceptor follow behind said coating means in the direction in which said coating means is moving.

2. An inspecting device as claimed in claim 1, wherein said photoreceptor comprises a photodetector held in a holder and a light-excluding bobbin adjustably movable along an optical axis of said photodetector, and an end of said light-excluding bobbin is provided adjacent to a surface of said material being treated.

3. An inspecting device as claimed in claim 1 or 2, wherein said electric circuit part comprises a drive part being amplitude modulated for permitting a light-emitting element to emit light by applying an electric current thereto; a bandpass filter matched to a frequency of said amplitute modulation of said drive part for obtaining output produced by said light-emitting element from the output of said photodetector; and a comparator for comparing output from the band-pass filter with a reference value and for generating said control signal.

4. An inspecting device as claimed in claim 1, wherein said control signal is adapted to be prevented from being produced when said projector and photoreceptor are off said trace of the thin film coating material which is being applied to said material being treated.

* * * * *